United States Patent
Mathew et al.

(10) Patent No.: US 12,351,701 B2
(45) Date of Patent: Jul. 8, 2025

(54) SYNTHETIC RUBBER LATEX COMPOSITIONS WITH IONIC LIQUID FOR ELASTOMERIC GLOVES

(71) Applicant: P.T. Medisafe Technologies, Medan (ID)

(72) Inventors: Monichan Puthuvelil Mathew, Kuala Lumpur (MY); Asish Kumar Sharma, Medan (ID)

(73) Assignee: P.T. Medisafe Technologies, Medan (ID)

(*) Notice: Subject to any disclaimer, the term of this patent is extended or adjusted under 35 U.S.C. 154(b) by 1024 days.

(21) Appl. No.: 17/325,718

(22) Filed: May 20, 2021

(65) Prior Publication Data
US 2021/0363326 A1 Nov. 25, 2021

Related U.S. Application Data

(60) Provisional application No. 63/029,001, filed on May 22, 2020.

(51) Int. Cl.
*C08K 5/3445* (2006.01)
*A41D 19/00* (2006.01)
(Continued)

(52) U.S. Cl.
CPC ........ *C08K 5/3445* (2013.01); *A41D 19/0082* (2013.01); *A61B 42/10* (2016.02);
(Continued)

(58) Field of Classification Search
CPC ............. A41D 19/0062; A41D 19/0082; A61B 42/10; C08J 2309/04; C08J 2309/08;
(Continued)

(56) References Cited

U.S. PATENT DOCUMENTS

| 5,998,512 A | * 12/1999 | Schloman ................. C08C 1/04 524/18 |
| 2008/0034467 A1 | 2/2008 | Chou et al. |

(Continued)

FOREIGN PATENT DOCUMENTS

| CN | 105462006 | * 4/2017 |
| CN | 105462006 B | 4/2017 |

(Continued)

OTHER PUBLICATIONS

Amit Das, "Ionic Modification Turns Commercial Rubber into a Self-Healing Material," ACS Appl. Mater. Interfaces 2015, 20623-20630.

(Continued)

*Primary Examiner* — Yan Lan
(74) *Attorney, Agent, or Firm* — Kwan & Olynick LLP

(57) ABSTRACT

Provided are compositions and associated methods for producing elastomeric rubber gloves with improved strength and flexibility at desirable glove palm thicknesses. An example elastomeric rubber glove comprises a substrate formed from a composition comprising a synthetic rubber latex, and an ionic liquid. The ionic liquid may comprise a combination of one or more alkyl imidazole ionic salts. The composition may comprise one or more metal oxides, including at least one of zinc oxide, magnesium oxide, cadmium oxide, and aluminum oxide. The synthetic rubber latex compositions were found to yield a material with strength and flexibility characteristics comparable to natural latex gloves of a greater thickness. The described gloves may also be cured without the addition of Sulphur and other vulcanization or rubber accelerators, further reducing the risk of allergies and costs of production.

16 Claims, 4 Drawing Sheets

(51) Int. Cl.
*A61B 42/10* (2016.01)
*C08J 5/02* (2006.01)
*C08K 3/22* (2006.01)
*C08L 9/04* (2006.01)
*C08L 9/08* (2006.01)
*C08L 9/10* (2006.01)
*C08L 11/02* (2006.01)
*C08L 13/00* (2006.01)
*C08L 79/00* (2006.01)

(52) U.S. Cl.
CPC .................................. *C08J 5/02* (2013.01); *C08K 3/22* (2013.01); *C08L 9/04* (2013.01); *C08L 9/08* (2013.01); *C08L 9/10* (2013.01); *C08L 11/02* (2013.01); *C08L 13/00* (2013.01); *C08L 79/00* (2013.01); *C08J 2309/04* (2013.01); *C08J 2309/08* (2013.01); *C08J 2309/10* (2013.01); *C08J 2311/02* (2013.01); *C08J 2313/02* (2013.01); *C08K 2003/2227* (2013.01); *C08K 2003/2296* (2013.01); *C08L 2201/52* (2013.01); *C08L 2203/02* (2013.01)

(58) Field of Classification Search
CPC .......................... C08J 2309/10; C08J 2311/02; C08J 2313/02; C08J 2321/02; C08J 5/02; C08J 7/0427; C08J 7/126; C08K 2003/2227; C08K 2003/2296; C08K 3/22; C08K 5/3445; C08L 11/02; C08L 13/00; C08L 21/00; C08L 2201/52; C08L 2203/02; C08L 79/00; C08L 9/04; C08L 9/08; C08L 9/10
See application file for complete search history.

(56) References Cited

U.S. PATENT DOCUMENTS

2012/0283367 A1 11/2012 Minder et al.
2019/0150537 A1* 5/2019 Isobe ...................... C08K 3/22

FOREIGN PATENT DOCUMENTS

| CN | 107964246 A | 4/2018 |
| EP | 1086980 A1 | 3/2001 |
| WO | 2021234651 A1 | 11/2021 |

OTHER PUBLICATIONS

International Application Serial No. PCT/IB2021/054409, Search Report and Written Opinion mailed Aug. 24, 2021, 11 pgs.
Marcus Suckow, "Tuning the Properties and Self-Healing Behavior of Ionically Modified Poly(isobutylene-co-isoprene) Rubber," ACS Publications, 2017, 12 pages.

* cited by examiner

SYNTHETIC RUBBER LATEX COMPOSITIONS WITH IONIC LIQUID FOR ELASTOMERIC GLOVES

CROSS-REFERENCE TO RELATED APPLICATIONS

This application claims the benefit of U.S. Provisional Application No. 63/029,001, entitled "SYNTHETIC RUBBER LATEX COMPOSITIONS WITH IONIC LIQUID FOR ELASTOMERIC GLOVES," filed on May 22, 2020, which is incorporated by reference herein in its entirety for all purposes.

TECHNICAL FIELD

The present disclosure generally relates to elastomeric gloves, and more specifically, to synthetic rubber gloves for medical, industrial, and specialty applications, including surgical.

BACKGROUND

Elastomeric gloves, manufactured from natural and synthetic rubbers and other latex materials, are widely used in medical, industrial, and specialty applications. For medical applications, gloves play a critical role by providing health care workers or doctors protection against germs, viruses, microbes and prevent contamination from blood and other bodily fluids. The use of elastomeric gloves, traditionally made from natural rubber latex, can result in certain users developing Type I hypersensitivity due to the protein content of the natural rubber. Reported data suggest that the average prevalence of latex allergy worldwide remains 9.7%, 7.2%, and 4.3% among healthcare workers, susceptible patients, and the general population, respectively.

Consequently, synthetic rubber latexes which do not contain proteins, such as nitrile rubber, chloroprene rubber (CR), isoprene rubber (IR), and the like, have been used as substitutes for natural rubber latex for gloves. To reduce costs, synthetic glove manufacturers have limited raw material consumption by reducing overall glove palm film thickness and weight, often targeting 0.10 mm or below.

Such reduction in thickness, however, can often be associated with added complexity and inefficiencies during manufacture and problems such as weak or low strength and failure to meet criteria set by International Medical Gloves Standards. There remains a strong need for synthetic rubber latex compositions and manufacturing methods to efficiently produce gloves with reduced palm film thickness, at lower cost and providing high levels of comfort to the end user yet conforming or exceeding industry standards of strength, modulus, and elongation.

SUMMARY

The following presents a simplified summary of the disclosure in order to provide a basic understanding of certain embodiments of the disclosure. This summary is not an extensive overview of the disclosure and it does not identify key/critical elements of the disclosure or delineate the scope of the disclosure. Its sole purpose is to present some concepts disclosed herein in a simplified form as a prelude to the more detailed description that is presented later.

In general, embodiments of the present disclosure provide a glove with improved characteristics, as well as improved methods of manufacture. Specifically, an elastomeric rubber glove comprises a substrate formed from a composition. The composition comprises a synthetic rubber latex, and an ionic liquid.

The ionic liquid may be present in the composition between 0.05 to 1.5 parts per hundred rubber. The ionic liquid may comprise a combination of one or more alkyl imidazole ionic salts selected from the group consisting of: 1-Butylimidazole, 1-Methylimidazole, 1-Hexylimidazole, and Bromo-1-imidazole.

The composition may further comprise one or more metal oxides. The one or more metal oxides may include at least one of zinc oxide, magnesium oxide, cadmium oxide, and aluminum oxide. The one or more metal oxides may be present in the composition between 0 to 1.5 parts per hundred rubber. The composition may further comprise one or more functional materials, wherein the one or more functional materials include at least one of polycarbodiimides, arzidines, and epoxies. The composition may further comprise an anionic surfactant. The ionic liquid may comprise 1-Butylimidazole, and the composition may further comprise a combination of one or more of the following: zinc oxide and aluminum oxide.

The substrate may include a single wall thickness of less than 0.10 mm in a palm region of the glove. The substrate may include a modulus at 300% elongation (M300) lower than or equal to approximately 2.5 megapascals. The substrate may include a strength measured by a force at break exceeding 6 Newtons. The elastomeric rubber glove may further comprise a polymeric coating on an interior surface of the glove.

Other implementations of this disclosure include other systems and methods corresponding to the described compositions. For instance, in another aspect, which may include at least a portion of the subject matter of any of the preceding and/or following examples and aspects, a wearable article is provided which comprises a substrate formed from the described compositions. The wearable article may be an elastomeric rubber glove.

Also provided is a method of manufacturing the described gloves and wearable articles. The method comprises dipping a former into a coagulant bath comprising a synthetic rubber latex composition. The synthetic rubber latex composition comprises a synthetic rubber latex and an ionic liquid. The method further comprises removing the former from the coagulant bath to form a layer of substrate on the former.

The ionic liquid may be present in the synthetic rubber latex composition between 0.05 to 1.5 parts per hundred rubber. The synthetic rubber latex composition may further comprise one or more metal oxides. The one or more metal oxides includes at least one of zinc oxide, magnesium oxide, cadmium oxide, and aluminum oxide. The synthetic rubber latex composition may further comprise one or more functional materials. The one or more functional materials include at least one of polycarbodiimides, arzidines, epoxies.

The method may further comprise curing the layer of substrate at temperatures below approximately 130° C. The method may further comprise chlorinating an interior surface of the substrate such that the interior surface includes chlorination levels between 0 parts per million (ppm) and 600 ppm, and applying a polymeric coating onto the interior surface of the substrate.

These and other embodiments are described further below.

DETAILED DESCRIPTION

Figure 1:
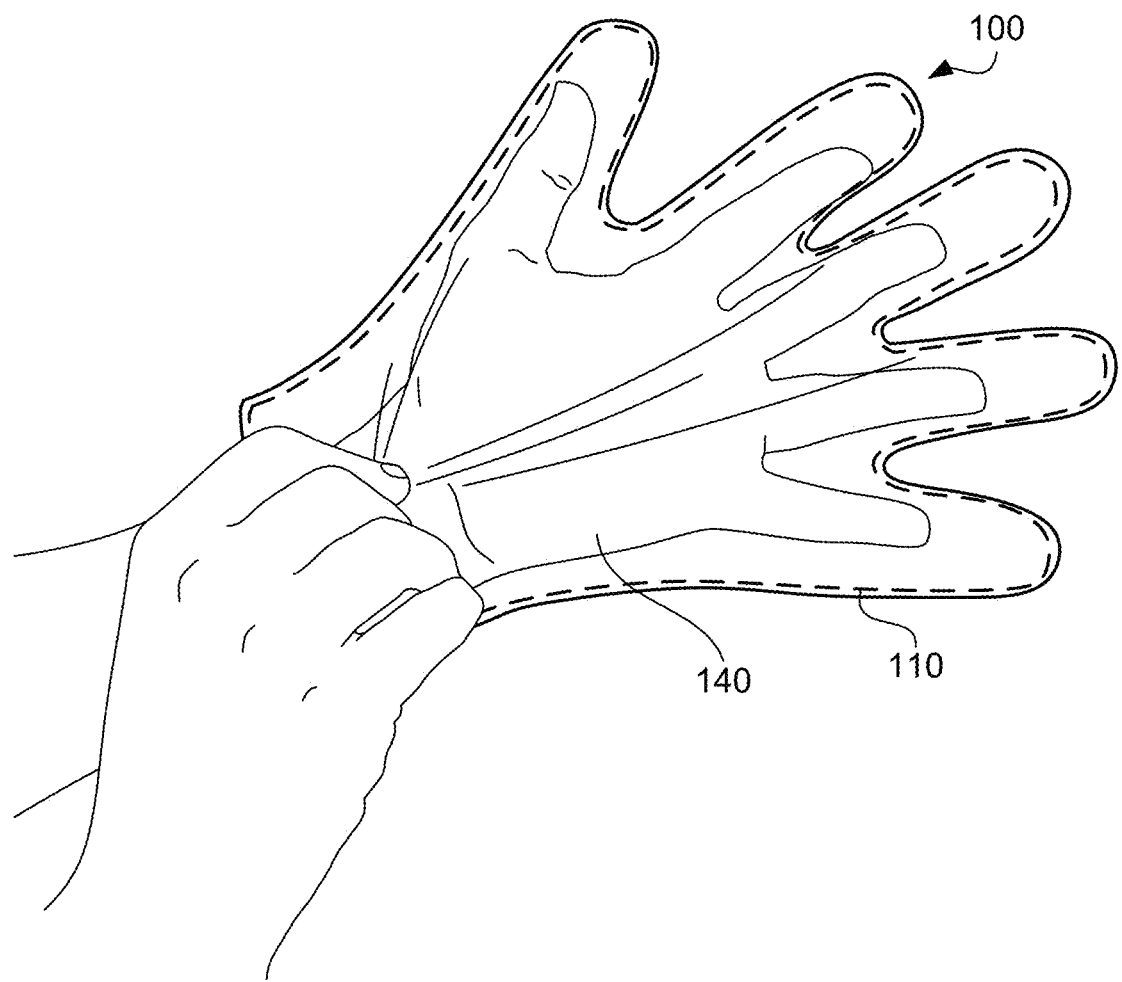
FIG. 1 illustrates an example wearable article formed from a synthetic rubber latex composition in accordance with one or more embodiments.

Reference will now be made in detail to some specific examples of the disclosure, including the best modes contemplated by the inventors for carrying out the disclosure. While the disclosure is described in conjunction with these specific embodiments, it will be understood that it is not intended to limit the disclosure to the described embodiments. On the contrary, it is intended to cover alternatives, modifications, and equivalents as may be included within the spirit and scope of the disclosure as defined by the appended claims.

For example, the systems and methods of the present disclosure will be described in the context of particular materials. However, it should be noted that the structure and mechanisms of the present disclosure may describe a variety and/or combination of different related and applicable elastomeric materials known in the art. As another example, the systems and methods of the present disclosure will be described in the context of particular wearable articles, such as gloves. However, it should be understood that the systems and methods are applicable to various other wearable articles that may be worn by users for various purposes.

In the following description, numerous specific details are set forth in order to provide a thorough understanding of the present disclosure. Particular example embodiments of the present disclosure may be implemented without some or all of these specific details. In other instances, well-known structures, mechanisms, and materials have not been described in detail in order not to unnecessarily obscure the present disclosure.

Overview

Elastomeric gloves, manufactured from natural and synthetic rubbers and other latex materials, are widely used in medical, industrial, and specialty applications. However, the use of elastomeric gloves made from natural rubber latex can result in certain users developing Type I hypersensitivity due to the protein content of the natural rubber. Reported data suggests that the average prevalence of latex allergy worldwide remains 9.7%, 7.2%, and 4.3% among healthcare workers, susceptible patients, and the general population, respectively.

Therefore, synthetic rubber latexes which do not contain allergenic proteins have been used as substitutes for natural rubber latex for glove applications. Such synthetic rubber latexes may include carboxylated acrylonitrile-butadiene rubber latex (xNBR), most often referred to as nitrile rubber, chloro-butadiene rubber latex most often referred to as chloroprene rubber (CR), methyl-butadiene rubber latex most often referred to as isoprene rubber (IR), and the like. Conventionally, gloves made from synthetic rubber latexes require levels of Sulphur and accelerators such as zinc dibutyl dithiocarbamate for curing and vulcanization purposes. However, utilizing a high level of curing/vulcanization chemicals, including Sulphur and accelerators or complex grafting chemistries and side-reactions often results in increased manufacturing or product costs and the potential for allergic reactions caused by residual accelerators (e.g., Type IV contact dermatitis).

As many glove applications are disposable in nature (e.g., medical examination gloves and surgical gloves), maintaining low product and production costs remains an important consideration. As a result, many synthetic glove manufacturers have targeted means to reduce raw material consumption by reducing the overall glove palm film thickness and resultant synthetic glove weight, often targeting 0.10 mm or below. Palm film thicknesses are measured according to ISO 11193-1:2008, which provides the specification for single-use medical examination gloves made from rubber latex or solution.

With a thinner synthetic elastomeric glove film, less force is needed to flex, stretch, or deform the article, creating a desirable softness and feel, providing the added benefit of greater comfort and tactile sensitivity to the user. Such improved comfort and flexibility also reduces or prevents hand fatigue during extended periods of use, particularly in the healthcare setting. However, reducing the thickness of the rubber film can often be associated with added complexity and inefficiencies during manufacture, as well as problems such as weak or low strength and failure during use. The strength of gloves for medical applications must meet the criteria set by International Medical Gloves Standards such as EN 455 (Medical gloves for single use—Part 2: Requirements and testing for physical properties) set by the European Committee for Standardization (CEN).

Improved dexterity and tactile sensitivity yet providing high strength of hand protection continues to be high on an end user's requirements. Furthermore, if the said methods produce gloves with all of these performance benefits coupled with the removal of known type I and type IV allergens, it opens a new generation of glove choice. As such, there remains a strong need for synthetic rubber latex compositions and manufacturing methods that produce gloves with a palm film thickness of 0.10 mm or below while maintaining a strength represented by a Force at Break (FAB) measurement exceeding 6.0 Newtons (N) as set forth by CEN EN455, as well as remaining soft and flexible as measured by modulus values in megapascals (MPa), tensile strength, and elongation at break values in percentage (%) comparable or lower than natural rubber latex gloves as measured by ASTM D412 Method A set by the American Society for Testing and Materials (ASTM). Typically, natural rubber latex gloves are represented by a modulus at 300% (M300) of equal or less than 2.0 MPa and elongation at break values greater than 800%.

The present disclosure describes novel synthetic rubber latex compositions and manufacturing methods for producing gloves with the aforementioned desired properties. The present disclosure presents and describes various characteristics of gloves made from example formulations described herein. Unless stated otherwise, FAB values are measured as per CEN EN455, whereas modulus, tensile strength, and elongation at break values are measured as per ASTM D412.

The described compositions and methods provide further advantages such as eliminating Sulphur and vulcanization and rubber accelerators, thereby reducing harmful chemicals, potential allergic reactions from users, and overall manufacturing costs. The described systems and gloves further provide a user with the increased strength of protection with high levels of comfort and dexterity so that delicate and nimble procedures can be performed with ease. As such, gloves manufactured with the described compositions and methods are CEN EN455 compliant with desirable softness and tactile properties as measured by modulus and elongation at break values comparable to, or better than, natural rubber values with palm film thicknesses of 0.10 mm or lower. In some embodiments, gloves with a palm film thickness of 0.05 mm or lower may be produced.

In particular, the disclosure describes a relatively thin synthetic elastomeric glove that is thinner and more pliable (or softer) than many conventional synthetic rubbers but designed still to retain the protective properties and critically provide enhanced strength and force at break (FAB) for all medical procedures in which synthetic rubber gloves are normally worn, as well as for industrial or laboratory work. Exemplary gloves include improved strength as measured by having an FAB of 6.0 Newtons (N) or greater, whilst maintaining a modulus at 300% (M300) of 2.5 MPa or below, and an elongation at break value equal to or greater than 800% at a glove palm film thickness below 0.10 mm for a single wall. As used herein, the "glove palm film thickness" may be referred to as single wall film thickness, which describes the thickness of a single layer of the glove, i.e., the thickness of a layer from the exterior of the glove to the interior.

In some countries, including the United States of America, gloves are required to have a minimum tensile strength of 14 MPa as set by ASTM D412 method A. As will be discussed, the described methods and compositions may provide gloves that meet such requirements. The described methods and compositions may also be implemented to provide gloves with thickness above 0.10 mm while retaining the aforementioned desired properties. For example, ISO 10282:2014 provides the specification for single-use sterile rubber surgical gloves and requires a minimum thickness of 0.10 mm. Such thicker gloves may be manufactured from the described compositions to include an FAB of 9.0 N and above, as required by CEN EN455, while including improved modulus and elongation at break values. These and other features result in novel compositions for synthetic rubbers latices being provided which are not anticipated, rendered obvious, suggested, or even implied by any prior art, either alone or in any combination thereof.

Example Embodiments

FIG. 1 illustrates an example wearable article formed from a synthetic rubber latex composition in accordance with one or more embodiments. With reference to FIG. 1, shown is glove 100 being donned on a user's hand 140. In various embodiments, glove 100 is an elastomeric rubber glove. For example, glove 100 may comprise a glove substrate manufactured from the compositions and methods described herein. In some embodiments, glove 100 may comprise an interior coating 110 (shown in dashed lines) applied to the interior surface of the glove substrate of glove 100, which contacts hand 140 of the user.

According to various embodiments, a synthetic rubber latex composition comprises a synthetic rubber latex, or blend thereof, combined with an ionic liquid formulation of an organic ionic liquid blended synergistically in water with metal oxides and other functional materials and process materials. As used herein, the term ionic liquid may be interchangeably referred to as ionic fluid. In various embodiments, the organic ionic liquid comprises one or more alkyl imidazole ionic salts such as 1-Butylimidazole, 1-Methylimidazole, 1-Hexylimidazole, and Bromo-1-imidazole. The metal oxides in the ionic liquid formulation may be any one or more of zinc oxide, magnesium oxide, cadmium oxide, aluminum oxide, and the like. As used herein, the term "functional materials" refers to compounds and other materials that include one or more cross-linkable groups. The functional (monofunctional, bifunctional, or polyfunctional) materials in the ionic liquid formulation may be any one or more of polycarbodiimides, arzidines, epoxies, and the like. The ionic liquid formulation may further comprise a combination of one or more process materials known in the art, including surfactants, pigments, dispersants, opacity agents, waxes, clays, antioxidants, fillers such as calcium carbonate, aluminum silicates, and alkalis such as potassium hydroxide.

In various embodiments, the ionic liquid is provided in liquid form at or about 98% purity. Surfactant is then added to the organic ionic liquid. In an example embodiment, the surfactant is an anionic surfactant, such as sodium dodecylbenzenesulfonate (SDBS) or sodium laureth sulfate (SLS), or a blend of the two, at a level up to a weight percent of 0.5% weight by weight (w/w). Once the ionic liquid is encapsulated with an emulsifier (surfactant), it is ready to be compounded with the synthetic rubber latex.

In various embodiments, the synthetic rubber latex, or blend thereof, is provided as a water-based mix. The desired components, including the metal oxides, functional materials, and other process materials (i.e., ZnO, $Al_2O_3$, carbodiimide, pigments, $TiO_2$, surfactant, antioxidants, wax, etc.) are added individually to the water-based mix of synthetic rubber latex with agitation. For example, each of the components may be added to the synthetic rubber latex as is or diluted with water to form a stable dispersion before being added to the synthetic rubber latex. The encapsulated organic ionic liquid may then be added to the synthetic rubber latex mixture to form the synthetic rubber latex composition. However, in some embodiments, the organic ionic liquid may be first blended with the metal oxides, functional materials, and other process materials before adding the water-based mix of synthetic rubber latex.

Water may then be added to dilute the composition to obtain the desired total solid content levels. A base may also be added to obtain the desired pH levels. The composition is then left with mixing before being used in the dipping line to produce the gloves. In certain embodiments, the organic ionic liquid may be present in the composition in an amount from 0.05 to 1.5 parts per hundred rubber (PHR). In an example embodiment, the organic ionic liquid is present at approximately 0.05 to 0.8 PHR. As another example, the organic ionic liquid is present at approximately 0.1 to 0.4 PHR. As described, the ionic liquid formulation may include organic ionic liquid, metal oxide, other crosslinking agents (functional materials), and other materials that aid in forming the glove (process materials). Such other materials may include one or more of the following: titanium dioxide, color pigment, surfactant, antioxidants, waxes. The synthetic rubber latex (or blend thereof) may be compounded with the ionic liquid by combining the said materials under controlled agitation, and the pH of the resulting synthetic rubber latex composition is raised to a range of approximately 9.0 to 11.5.

An example formulation (Example 1) for compounding with a synthetic rubber latex may include the materials in the ranges shown below in Table 1, with all levels listed in approximate parts per 100 parts of dry rubber (PHR):

TABLE 1

Example ionic liquid formulation (Example 1)

| Material | Amount (PHR) |
| --- | --- |
| Ionic Liquid (e.g. 1-Butylimidazole) | 0.05 to 1.5 |
| Metal Oxide (e.g. zinc oxide) | 0 to 1.5 |
| Mono-, bi-, or poly-functional material (e.g. polycarbodiimide) | 0 to 0.8 |
| Potassium Hydroxide (for pH adjustment) or ammonium hydroxide | 0.5 to 2.0 |
| Titanium Dioxide | 0 to 5.0 |
| Color Pigment | 0 to 1.0 |

The example formulation in Table 1 is not limited to the listed components and may include various other materials described herein in various embodiments. Various types, or combinations, of synthetic rubber and elastomers in a latex form, may be compounded with the described formulation in various embodiments. In various embodiments, the ionic liquid is present in the formulation between 0.05 to 1.5 PHR. In an example embodiment, the ionic liquid is present in the formulation at, or approximately at, 0.5 PHR.

The formulation can be adjusted in the ranges listed above to compensate for the inherent properties of the many different synthetic latexes and elastomers available. Examples may include carboxylated acrylonitrile-butadiene rubber latex (nitrile), polychloroprene latex, styrene-butadiene latices, acrylic latices, polyisoprene, latices of styrene-butadiene copolymers and block copolymers, polyurethane elastomer dispersions, and mixtures of the same. Some suitable synthetic rubber latex examples include NANTEX 660 from Nantex Ind. Co., Ltd, SYNTHOMER 6338 from Synthomer Sdn Bhd, POLYLAC 580N from Shin Foong, SD671A from Showa Denko, LM61 from Denka, NIPOL LX550L & NIPOL LX430 from Zeon Corp., CARIFLEX IR0401 from Kraton Corp., BSTS IRL501 & 701 from BST Specialty, and various blends of one or more of these examples. In some embodiments, the blends of synthetic latexes and elastomers may include various ratios of the described examples. For example a blend may comprise a 1:1 ratio, or 50% of one latex and 50% of a second latex. As another example, a blend may comprise 70% of one latex and 30% of another latex, or 80% of one latex and 20% of another latex. In some embodiments, other common rubber compounding materials such as waxes, clays, anionic and non-ionic surfactants, dispersants, and the like may also be added to the formulation.

The broad applicability of the described compositions concerning the choice of elastomers and synthetic rubber latices may be due to the nature of the ionic liquid being able to coordinate and crosslink ionically and covalently. Hence, with functionalized synthetic rubber latices such as nitrile rubber, ionic crosslinking may be most prevalent, whereas with other synthetic rubbers such as chloroprene or isoprene covalent crosslinking through the ionic liquid's alkyl group may be favored. The resulting properties of tested gloves, further described below, illustrate this behavior.

A wide range of metal oxides may also be used. Example zinc oxides may include white seal OCTOCURE 573 from Tiarco Chemical, BOSTEX 422 A from Sokachem, and/or active zinc oxide from Lanxess. An example of aluminum oxide may be DERLINK A102. A wide range of monofunctional, bifunctional, or polyfunctional materials can also be used. Examples of such functional materials may include ZOLDINE XL-29SE from Angus Chemical, M-GEN2-Type A & B from Midori Anzen Co. Ltd., and PERMUTEX XR5508, XR2500, and XR9181 from Stahl. In some embodiments, titanium dioxide is included to provide the desired level of whiteness or opaqueness, whereas the pigment is included to provide a desired final product color.

Of particular advantage, elastomeric gloves can be formed from the described compositions without using conventional Sulphur and accelerators, resulting in several improvements over existing elastomeric gloves. First, the risk of allergic reactions and dermatitis caused by such chemical additives is eliminated. Furthermore, rubbers (synthetic and natural), which comprise Sulphur-containing crosslinking agents and accelerators, typically have to be vulcanized at temperatures greater than about 130° C. However, a synthetic rubber latex glove manufactured with the described compositions can be cured at temperatures less than about 130° C. reducing energy consumption and production costs. In some embodiments, rubber latex comprising the described compositions can be sufficiently cured at temperatures less than 120° C. and more particularly at temperatures less than 110° C.

According to the present invention, by simultaneously controlling the level of organic ionic liquid with the other materials in the composition, along with the glove thickness, both variables may be tuned to maximize material strength and minimize the force needed to stretch the material. Synthetic rubber latex compositions produced with the example ionic liquid formulations were found to yield a material with force response behavior similar to a natural latex glove of a greater thickness. The crosslinking is controlled by the type and amount of organic ionic liquid, metal oxides, and the other functional (monofunctional, bifunctional, or polyfunctional) materials added to the synthetic rubber latex before it is used to produce the glove. The thickness of the glove can be controlled by various means during the dipping process but most commonly by the rubber latex total solids content (TSC) and the coagulant concentration (weight %). Thus, the described compositions and methods maximize the strength potential of the synthetic rubber while still producing a glove that is more pliable and more comfortable to wear than conventional synthetic-made articles.

In general, crosslinking of synthetic rubber and the vulcanization process involves converting a weak rubber with low wet gel strength to rubber with good strength and elasticity through the formation of a three-dimensional network of crosslinks. Crosslinks are formed conventionally in at least two ways: 1.) the diene or vinyl subunits within the rubber's backbone can be covalently crosslinked with Sulphur/accelerator systems, and 2.) the functional groups (e.g., carboxylate from an organic acid incorporated with the synthetic rubber during synthesis by the manufacturer) can be ionically crosslinked with metal oxides or salts. Many currently available rubber formulations generally employ a combination of these two curing mechanisms. For example, manufacturers frequently recommend the addition of 1 to 10 parts of a metal oxide (such as zinc oxide) per 100 parts of rubber (PHR), as well as Sulphur levels of 1-4 parts per 100 parts of rubber (PHR) and accelerator levels of 0.5 to 1.5 parts per 100 parts of rubber (PHR).

With the use of an organic ionic liquid, the described compositions may proceed with the same or a different form to the above crosslinking routes but with much lower metal oxide levels and without the need for Sulphur and traditional vulcanization agents and accelerators, thereby reducing materials costs, as well as the amount of potential allergens in the final product. The particular properties arise, at least in part, from the nature of the ionic liquid and how it combines synergistically with the other materials and its efficient interaction with available crosslinking sites within the synthetic rubber's carbon chain or backbone. Ionic liquids are a class of purely ionic salt-like materials in a liquid form comprising organic cations (such as imidazolium, ammonium, pyrrolidinium, piperidinium, phosphonium, and sulfonium) associated with inorganic anions (Cl—, AlCl4-, PF6-, BF4-, NTf2-, DCA-, etc.) or organic anions (CH3COO—, CH3SO3-, etc.). As previously described, the organic ionic liquid may comprise alkyl imidazole ionic salts, including one or more of the following: 1-Butylimidazole, 1-Methylimidazole, 1-Hexylimidazole, and Bromo-1-imidazole. In certain embodiments, the organic ionic liquid comprises 1-Butylimidazole as the alkyl imidazole ionic salt.

Table 2 compares example ionic liquid formulations (Examples 2, 3, 3a, and 4) against control formulations (C1, C2, C3, and C4) without ionic liquid previously known in the art.

TABLE 2

Comparison of Example Formulations

| | Controls | | | | Examples | | | | | |
| --- | --- | --- | --- | --- | --- | --- | --- | --- | --- | --- |
| | C1 | C2 | C3 | C4 | 2 | 2a | 3 & 3a | 3b | 4 | 4a |
| Ionic Liquid (e.g. 1-Butyl imidazole) (PHR) | — | — | — | — | 0.2 | 0.3 | 0.2 | 0.3 | 0.2 | 0.2 |
| Zinc Oxide (PHR) | 4.8 | 1.2 | — | 0.15 | — | 0.2 | 0.6 | 0.5 | 0.15 | 0.1 |
| Aluminum Oxide (PHR) | — | — | 2.0 | 0.75 | 0.65 | 0.5 | — | — | 0.65 | 0.5 |
| Functional Materials (PHR) | — | — | — | — | 0.2 | — | — | — | 0.2 | 0.2 |
| Sulphur (PHR) | 3.0 | 0.8 | — | — | — | — | — | — | — | — |
| Vulcanization Accelerators (PHR) (e.g. 50/50 ZDBC/ZDEC) | 1.0 | 0.7 | — | — | — | — | — | — | — | — |

As shown, control formulations C1, C2, C3, and C4 do not include ionic liquid. Control formulations C1 and C2 include different levels of zinc oxide along with traditional Sulphur and accelerators, while the example formulations including ionic liquid do not include such components. Such accelerators include zinc dibutyl dithiocarbamate (ZDBC) and/or zinc diethyl dithiocarbamate (ZDEC). Additional control formulations C3 and C4 also did not include such Sulphur and accelerators. Control C3 included aluminum oxide, while control C4 includes both zinc oxide and aluminum oxide.

Example formulations 2, 2a, 3, 3a, 3b, 4, and 4a included 1-Butyl Imidazole as the organic ionic liquid and were used to form the tested gloves. Example 2 included aluminum oxide along with polycarbodiimide as a functional material. Example 2a included both zinc oxide and aluminum oxide. Examples 3, 3a, and 3b included zinc oxide and no monofunctional, bifunctional or polyfunctional materials. Formulation 3b was combined with a first combination of synthetic rubber latexes for Example 3b-1 and combined with a second combination of synthetic rubber latexes for Example 3b-2. Finally, Examples 4 and 4a included a combination of zinc oxide and aluminum oxide for metal oxides along with polycarbodiimide as a functional material. The example formulations in Table 2 are not limited to the listed components and may include various other materials described herein in various embodiments. The properties of the resultant elastomeric gloves manufactured from the aforementioned formulations are described in Table 3 below.

TABLE 3

Glove Properties manufactured from formulations described in Table 2

| | Palm Thickness (mm) | Force at Break (FAB) (N) | Modulus M300 | Elongation at Break (%) | Tensile Strength (per ASTM D412) (MPa) |
| --- | --- | --- | --- | --- | --- |
| Control C1 | 0.09 | 4.6 | 2.7 | 688 | 17.4 |
| Control C2 | 0.09 | 4.2 | 2.2 | 784 | 16.8 |
| Control C3 | 0.10 | 2.7 | 3.1 | 725 | 14.9 |
| Control C4 | 0.09 | 5.2 | 2.2 | 774 | 21.2 |
| Example 2 | 0.08 | 6.1 | 1.8 | 849 | 18.9 |
| Example 2a | 0.09 | 7.5 | 1.6 | 935 | 16.8 |
| Example 3 | 0.10 | 6.0 | 2.1 | 822 | 20.8 |
| Example 3a | 0.09 | 6.3 | 1.8 | 828 | 18.5 |
| Example 3b-1 | 0.09 | 6.1 | 2.0 | 794 | 20.6 |
| Example 3b-2 | 0.10 | 6.2 | 1.7 | 878 | 18.7 |
| Example 4 | 0.09 | 7.0 | 1.6 | 829 | 17.1 |
| Example 4a | 0.09 | 6.5 | 1.5 | 922 | 22.5 |

Table 3 shows, for each glove, the single wall palm thickness measured in millimeters (mm), the force at break (FAB) measured in Newtons (N), the modulus at 300% (M300) measured in megapascals (MPa), tensile strength measured in megapascals (MPa), and an elongation at break measured as a percentage (%) of increased length of the initial length after breakage of the tested glove at a controlled temperature.

As illustrated in Tables 2 and 3, gloves manufactured according to the described example formulations include a palm thickness for a single wall of 0.10 mm and below without sacrificing strength; the measured force at break (FAB) characteristics are commensurate with those typically associated with thicker gloves of a heavier weight basis. "Strength" as used herein can be described as a function of the amount of force necessary to break a sample of prescribed shape and dimensions, such as measured by CEN EN455 standards. As compared with gloves manufactured with the control formulation, the example formulations resulted in gloves with improved FAB, modulus, tensile strength, and elongation characteristics.

As further shown in Table 3, gloves manufactured from example formulations include a thickness of about 0.08 to 0.10 mm for a single wall of latex film in the palm area, a force-at-break (FAB) reading of between 6.1 and 7.0 N with an elongation at break value greater than 800/6 and a modulus at 300% (M300) in a range from 1.6 to 2.1 MPa. Thus, the described composition may be used to produce gloves with an M300 of 2.5 MPa or below. As shown in Table 3, in some embodiments, the M300 of produced gloves may be lower than 2.0 MPa. This compares very favorably with modulus and elongation at break values of natural rubber (NR) latex gloves and even more favorably based on palm thickness as NR latex gloves tend to be 0.18 mm or greater.

Maintaining the thinness of the elastomeric synthetic rubber gloves can enhance tactile sensitivity, and significantly increase user comfort and reduce hand fatigue. Production and product costs can also be reduced. A thinner glove can help lower costs in manufacturing because of the relatively less material needed compared to thicker gloves. Furthermore, the described methods utilize lower temperatures of vulcanization and curing than the traditional processes, resulting in a more energy-efficient process and additional savings in production costs. Additionally, a larger number of thinner gloves can be packaged into a standard dispenser resulting in less packaging and waste. Furthermore, as elastomeric gloves tend to be of single-use, reducing the amount of synthetic rubber incorporated (while meeting the appropriate standards as described within this invention) provides a significant environmental benefit by reducing disposal waste at hospitals and other places of use.

In some embodiments, gloves may be manufactured with a minimum glove palm single wall thickness of 0.10 mm or more to meet standards for surgical gloves (ISO 10282: 2014). Such thicker gloves may include a FAB of 9.0 N or greater (as required by CEN EN455) while maintaining improved modulus and elongation at break values than conventional gloves of the same or comparable thickness. This would provide adequate protection while drastically improving tactile sensitivity and user comfort, such as during operations or procedures requiring manual dexterity for prolonged periods.

Additional testing shown in Table 4 illustrates the effect of the ionic liquid in the formulation. In the experiment, gloves produced using a synthetic rubber latex composition including ionic liquid were compared with gloves produced using a similar synthetic rubber latex composition without ionic liquid.

Glove B was formed from a synthetic rubber latex composition, including the ionic liquid formulation of example 3a described in Table 2. Glove C was formed from a synthetic rubber latex composition, including the ionic liquid formulation of example 2a described in Table 2. Instead of an ionic liquid formulation, glove A was formed from a synthetic rubber latex composition, including control formulation C4 without ionic liquid described in Table 2, which included aluminum oxide at 0.75 PHR and zinc oxide at 0.15 PHR. Glove A2 was formed from another composition, including control formulation C3 without ionic liquid as described in Table 2.

The results shown in Table 4 confirm that the inclusion of the organic ionic liquid within the described synthetic rubber composition has a clear impact on the strength and softness of the formed glove. With regards to strength, glove B displayed an increased force at break of 1.1 Newtons compared to glove A. With respect to softness and flexibility, glove B displayed an increase in elongation at break value and reduced modulus at 300%. Notably, the presence of ionic liquid significantly improves the strength of the glove but does not impact the softness indicated by modulus and elongation at break. Typically, when strength is improved through known crosslinking systems (e.g., metal oxides), a corresponding stiffening of the glove is observed, indicated by an increase in M300 values and a decrease of elongation at break values. Here, gloves B and C indicate that compositions including ionic liquid form more robust gloves that maintain excellent softness values compared to the gloves A1 and A2 made from control formulations without ionic liquid, at the same thickness.

Additional testing shown in Table 5 further illustrates the softness characteristics of gloves formed with the example formulations. In the experiment, gloves produced using a synthetic rubber latex composition described in Table 2, including ionic liquid, were compared with gloves produced using a similar synthetic rubber latex composition described in Table 2 without ionic liquid.

TABLE 5

Softness of the Gloces manufactured from Formulations described in Table 2 as defined by Modulus Values

|  | Modulus M100(MPa) | Modulus M300 (MPa) | Modulus M500 (MPa) | Elongation at Break (%) |
| --- | --- | --- | --- | --- |
| Control C1 | 1.1 | 2.7 | 9.5 | 688 |
| Control C2 | 0.4 | 2.2 | 8.1 | 784 |
| Example 2a | 1.1 | 1.6 | 2.4 | 935 |

TABLE 4

Glove Properties Prepared from an Example Composition with and without Ionic Liquid Present

|  | Palm Thickness (mm) | FAB (N) | M300 | Elongation at Break (%) |
| --- | --- | --- | --- | --- |
| Glove A1 - Control C4 (No Ionic Liquid Present) | 0.09 | 5.2 | 2.2 | 774 |
| Glove A2 - Control C3 (No Ionic Liquid Present) | 0.10 | 2.7 | 3.1 | 725 |
| Glove B - Example 3a (Ionic Liquid Present at 0.2 PHR) | 0.09 | 6.3 | 1.8 | 828 |
| Glove C - Example 2a (Ionic Liquid Present at 0.3 PHR) | 0.09 | 7.5 | 1.6 | 935 |

TABLE 5-continued

Softness of the Gloves manufactured from Formulations described in Table 2 as defined by Modulus Values

| | Modulus M100(MPa) | Modulus M300 (MPa) | Modulus M500 (MPa) | Elongation at Break (%) |
|---|---|---|---|---|
| Example 2b | 0.5 | 2.2 | 3.4 | 868 |
| Example 3 | 0.4 | 2.1 | 4.3 | 822 |
| Example 3a | 0.5 | 1.8 | 3.2 | 828 |
| Example 3b-2 | 1.4 | 1.7 | 2.6 | 878 |
| Example 4 | 1.4 | 1.6 | 2.6 | 829 |

Figure 2A:
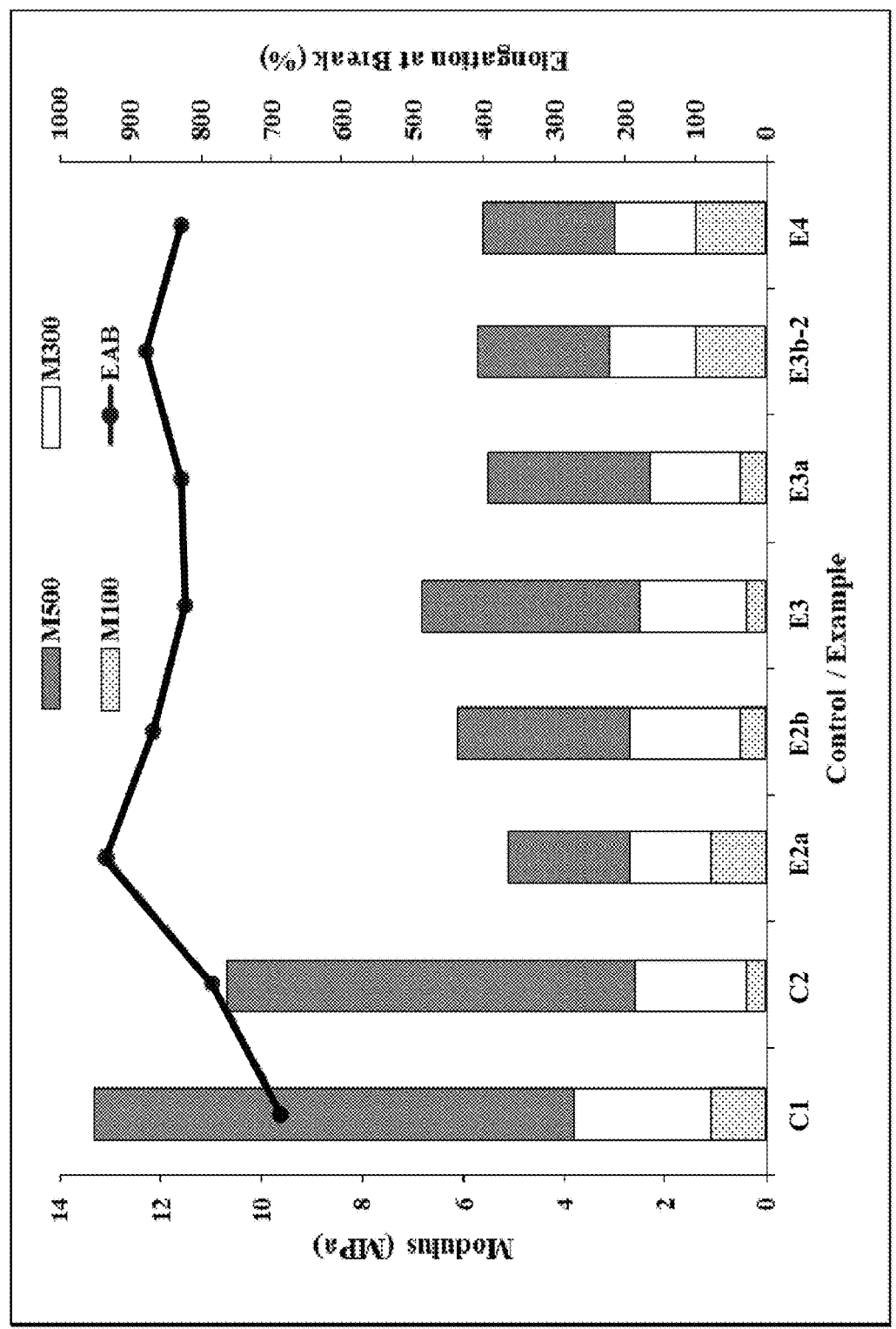
FIGS. 2A and 2B illustrate graphical representations of results shown in Table 5.
Figure 2B:
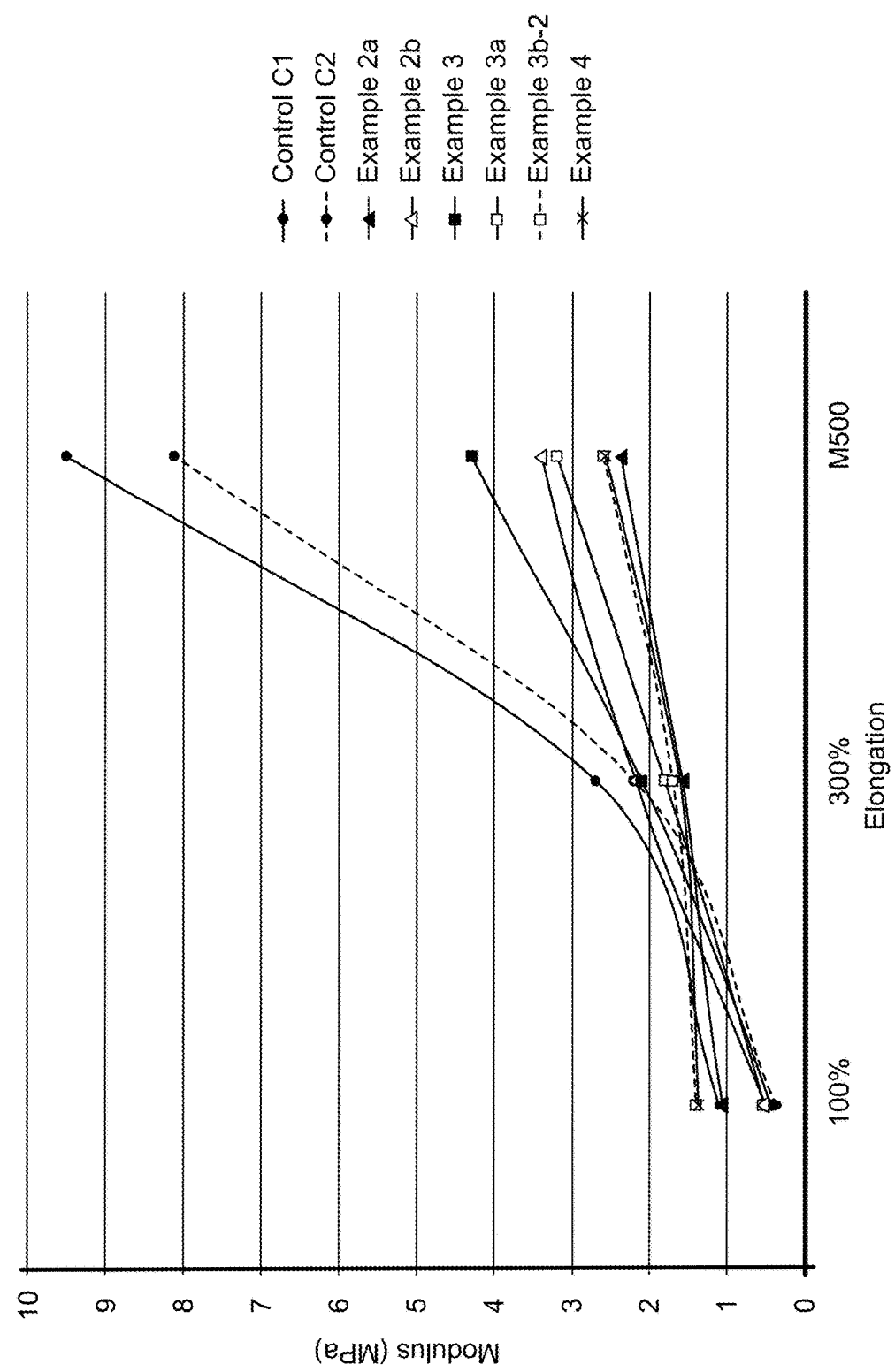

A more comprehensive profile of modulus values is provided in Table 5. In particular, values for modulus of gloves at 100% (M100) and 500% (M500) elongation were measured along with the M300 values previously discussed. These characteristics are further shown in FIGS. 2A and 2B illustrating graphical representations of results shown in Table 5. Graph 201 in FIG. 2A shows a bar chart of the modulus values of gloves made from the formulations shown in Table 5. The bar chart indicates that gloves made from all formulations have comparable M100 and M300 values with control formulation C1 resulting in the highest M300 value. The bar chart further shows much lower values for M500, the modulus at 500% elongation, for gloves formed from example formulations including ionic liquid, while control formulations without ionic fluid resulted in gloves with the highest M500 values.

Graph 202 in FIG. 2B illustrates another representation of the force required to stretch the gloves up to 500% increases in length. As shown by graph 202, the modulus values for gloves made from example formulations 2a, 2b, 3, 3a, 3b-2, and 4 show a much more gradual and shallow increase in values from M100 through M300 and up to M500. Whereas control formulations C1 and C2 show a much more significant increase from M300 to M500 values, indicating much higher stiffness at greater elongation levels.

The ionic liquid formulations also resulted in greater elongation at break values. From graph 201 and Table 5, it is evident that the example formulations resulted in gloves that broke at above 800% elongation. In contrast, the control formulations C1 and C2 without ionic liquid resulted in gloves that broke at 688% and 784% elongation. This is consistent with the control formulations causing higher stiffness at greater elongation levels shown by the modulus measurements.

This further suggests that the mechanism or mode of crosslinking for the ionic liquid formulations differs from existing vulcanization chemicals such as Sulphur and accelerators. This also suggests that the ionic liquid formulations may result in gloves with greater tear strength or force required to tear the material. Tear strength was measured for gloves formed with formulation 3b-2 and control formulation C1 according to ASTM D624 standards. The glove formed with formulation 3b-2 generated a tear strength of 27.4 KN/m compared to a tear strength of 25.0 KN/m measured for the glove formed with control formulation C1.

Stress relaxation values of gloves formed with the example formulations were also tested with the results shown in Table 6 below. Stress relaxation values were measured as per the ASTM D412 standard.

TABLE 6

Stress Relaxation Property of the Gloves Manufactured from Formulations described in Table 2

| | Stress Relaxation (%) |
|---|---|
| Control C1 | 54.8 |
| Control C2 | 55.7 |
| Control C3 | 46.8 |
| Example 3 | 56.1 |
| Example 3a | 57.1 |
| Example 3b-1 | 59.8 |
| Example 3b-2 | 56.1 |
| Example 4 | 58.8 |
| Example 4a | 60.0 |

Stress relaxation is an important parameter that can, together with modulus, characterize the elastic rubber performance and the tactile sensation of a glove. The higher the percentage stress relaxation value, the better the glove will fit the shape of a user's hand, and the more elastic it feels with less creep experienced. Significant creep is undesirable as the glove becomes loose after extended use, impacting the performance and productivity, and costs if replacement gloves are needed.

However, when a high-stress relaxation value is combined with a high modulus value (i.e., M300>2.5 MPa), it is known that such glove would quickly cause finger fatigue. It is imperative in medical and surgical uses that the gloves fit closely on the hand and in the finger and palm regions. It is customary for users to wear gloves of slightly smaller dimensions than their hands to ensure a close, snug fit. However, discomfort can arise during the use of these gloves, from continued application of pressure by the glove on the hand if the glove is too stiff. Commonly, gloves formed from prior art formulations with synthetic nitrile-butadiene rubber exhibit low stress relaxation (less than 50%) and a much higher modulus at 300% (>7 MPa). Consequently, end-users of such prior art gloves often complain of hand fatigue with synthetic gloves of the prior art.

The results of Table 6 demonstrate that formulations with ionic liquid improve the stress relaxation of the formed gloves with values ranging from 56% to 60%, indicating such gloves will feel more elastic and will fit more snugly to the hand compared to gloves made from control formulations C1, C2, and C3 (without ionic liquid) and which rely on metal oxides alone, or in combination with Sulphur and accelerators, for crosslinking. Thus, the example formulations produce favorable stress relaxation properties with values approaching 60% and a low modulus (approximately <2.0 MPa), but critically with high strength and FAB values (FAB >6N). As such, gloves formed with the example formulations described herein result in more comfortable and better fitting gloves allowing for improved touch sensitivity on extended wearing compared with prior art gloves with low stress retention of less than 50%.

Glove properties before and after aging were also tested with the results shown in Table 7 below. FAB was measured as per EN455. M300, M500, elongation at break, and tensile strength values were measured as per ASTM D412.

TABLE 7

Glove Properties Manufactured from Formulations described in Table 2 (Before and After Aging at 70° C. for 7 days)

| Control/ Example | Force at Break # (N) | | Modulus M300 (MPa) | | Modulus M500 (MPa) | | Elongation at Break (%) | | Tensile Strength (MPa) | |
|---|---|---|---|---|---|---|---|---|---|---|
| | Bef. | Aft. | Bef. | Aft. | Bef. | Aft. | Bef. | Aft. | Bef. | Aft. |
| C1 | 4.6 | 5.5 | 2.7 | 4.7 | 9.5 | 10.5 | 688 | 518 | 17.4 | 21.6 |
| C2 | 4.2 | 4.9 | 2.2 | 4.2 | 8.1 | 8.9 | 784 | 637 | 16.8 | 20.3 |
| 2a | 7.5 | 6.4 | 1.6 | 1.6 | 2.4 | 2.8 | 935 | 818 | 16.8 | 19.9 |
| 2b | 7.3 | 7.7 | 2.2 | 2.6 | 3.4 | 3.9 | 868 | 834 | 20.8 | 25.0 |
| 3 | 6.0 | 7.7 | 2.1 | 2.3 | 4.3 | 4.6 | 822 | 776 | 20.8 | 22.0 |
| 3a | 6.3 | 7.6 | 1.8 | 2.5 | 3.2 | 3.7 | 828 | 876 | 18.5 | 21.3 |
| 3b-2 | 6.2 | 6.2 | 1.7 | 2.1 | 2.6 | 4.6 | 878 | 628 | 18.7 | 20.8 |
| 4 | 7.0 | 8.1 | 1.6 | 2.1 | 2.6 | 3.2 | 829 | 753 | 17.1 | 18.3 |

Critically a glove must age well, with minimum requirements of an aged elongation >400% and aged tensile strength >14 MPa as governed by ASTM. Gloves formed from existing formulations, which rely on high zinc oxide and Sulphur and accelerators (e.g., control formulation C1 in Table 7), can often lead to accelerated aging and poor product storage performance. This is characterized by increasing tensile strength but a significant increase in modulus and alarming reduction in elongation after aging, as shown in Table 7.

The aging experimentation proves that the example formulations maintain strong tensile strength and force at break after aging while showing good aging resistance. Gloves formed from formulations 2a, 2b, 3, 3a, 3b-2, and 4 all result in negligible changes in modulus and elongation after aging. The tensile strength and elongation of such gloves are well above the ASTM requirements for medical gloves before and after aging. Consequently, such gloves will not deteriorate in performance during storage and may be classified as having an excellent shelf life.

Methods of Manufacture

Figure 3:
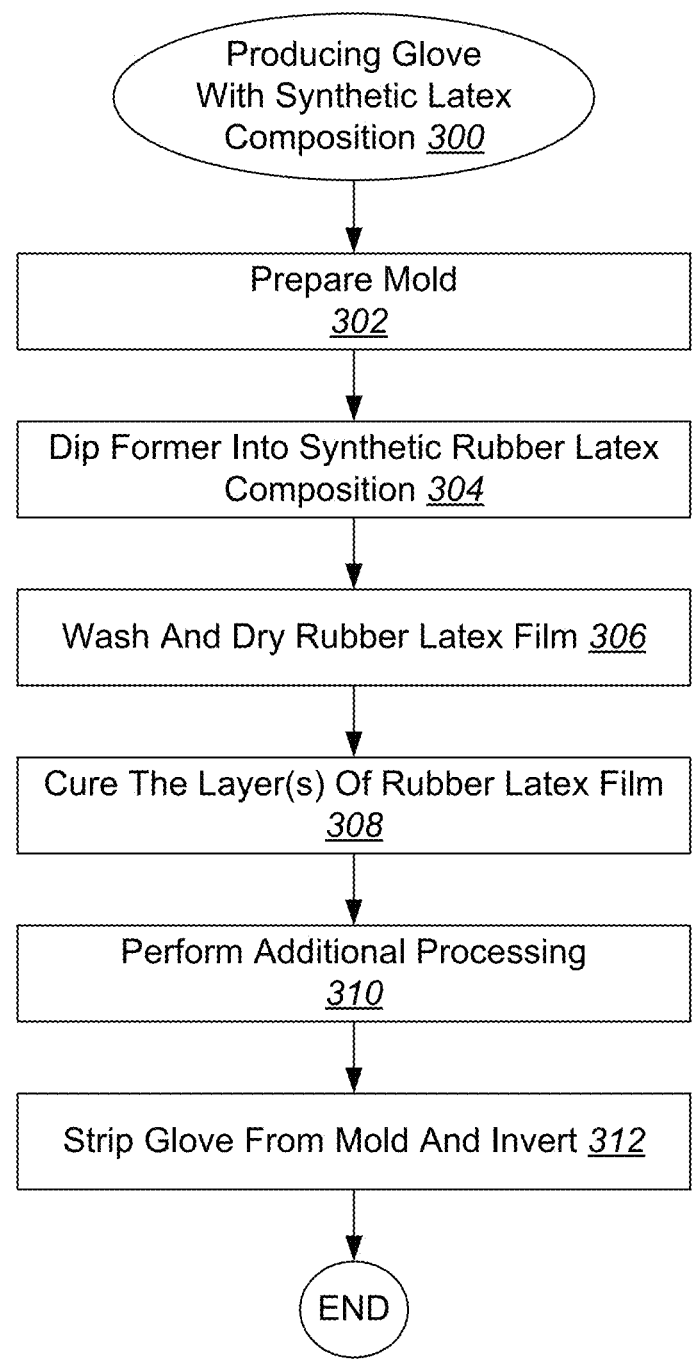
FIG. 3 illustrates an example method for producing a glove with the described synthetic rubber latex compositions, in accordance with one or more embodiments.

With reference to FIG. 3, shown is an example method 300 for producing a glove with the described synthetic rubber latex compositions, in accordance with one or more embodiments. At operation 302, a former or mold made from ceramic or a composite polymer in a desired shape and size is first washed, cleaned, and dried. For example, the former may be an anatomical former configured with a geometric profile corresponding to a human hand.

The clean former may then be preheated and then dipped or immersed into a coagulant bath. In certain embodiments, the former is heated to approximately 55-60° C. (such as 58° C.). The former is then withdrawn from the coagulant bath and then dried, leaving a coagulant such as calcium nitrate or calcium chloride on the surface of the former. For example, the coagulant bath may comprise an aqueous calcium nitrate solution at a solids content of 18-20% containing 2.5-3.5% coagulant powder-free (CPF) such as CYCLERON 345 at pH 6.5 to 7.2.

Next, at operation 304, the former, with coagulant on its surface, is dipped into a bath of the synthetic rubber latex composition. As previously discussed, in various embodiments, the synthetic rubber latex composition may comprise a synthetic rubber latex or blends thereof, water, an organic ionic liquid, metal oxides, and other functional (monofunctional, bifunctional, or polyfunctional) materials. The composition may further comprise process materials known in the art such as surfactants, pigments, dispersants, opacity agents, waxes, clays, antioxidants, fillers such as calcium carbonate, aluminum silicates, and alkalis such as potassium hydroxide. The coagulant-coated former is dipped or immersed into the composition and withdrawn, leaving a thin layer of the synthetic rubber on the former and forming a thin layered gelled glove. In some embodiments, a bead can be rolled at the top of the glove cuff.

Once withdrawn from the synthetic rubber latex composition, the coagulated wet rubber layer is partially dried so that the film gains strength before entering a series of pre-leach tanks where water is continuously replenished to leach and wash the film at operation 306. For example, the mold with the gelled glove rubber may be dried in ovens at a temperature in the range of about 80° C. to 100° C. and next immersed in clean, continuously circulated water to remove all of the water-soluble material components from the gelled rubber glove. The synthetic rubber layer on the mold is then dried or partially dried to further reduce the water content.

Compared to existing manufacturing methods, the solids content of the synthetic rubber latex (or blend thereof) is reduced from 40-65% to approximately 19-22% to provide control over the thickness of the glove employing a coagulant dipping process using single and double former lines. Reducing the solids content also contributes to the improved quality of the synthetic rubber film acquired on the former.

Method 300 encompasses the preparation of single-layered or multiple-layered elastomeric films. Thus, in some embodiments, operation 304 is repeated to dip the former with the partially dried synthetic rubber layer into the synthetic rubber latex solution to acquire additional layers of synthetic rubber onto the former. Operation 304 may be repeated any number of times to obtain the desired amount of layers before being washed at operation 306. For example, the additional thickness may be desired to meet the requirements set for surgical gloves. Additional thickness may also be achieved by increasing the dwell time of the former within the composition or adjusting the composition's viscosity via rubber latex total solids content (TSC) and the coagulant concentration (weight %).

Once the desired amount of layers of synthetic rubber is formed on the former and have been sufficiently washed, the one or more layers of elastomeric synthetic rubber on the former are dried and cured (vulcanized) at operation 308. As previously described, the use of the described synthetic rubber latex compositions allows the glove to be cured without Sulphur or other accelerators and at temperatures less than about 130° C., which is lower than existing gloves.

When the former with the gelled rubber substrate is then heated at these higher temperatures, the remaining water content is removed, and the ionic liquid and, if present metal oxide, other crosslinking agent combine and form a 3-dimensional crosslink network with the available sites in the synthetic rubber main chain or backbone.

At operation 310, the formed elastomeric article or glove can optionally undergo further processing such as chlorination to reduce tack and/or an inner polymeric glove coating application. For example, the polymer coating may be commercially available FLEXICOAT 892 or FLEXICOAT 168N at 2-4% TSC. As another example, an inner polymeric glove coating may comprise a polymer system of emulsion polymers, including a combination of one or more polymer and/or monomer latices with an average particle size in the range of approximately 100 to 400 nanometers (nm), as well as a larger particle-sized polymer with an average particle size above 500 nm. The polymers of smaller particle size may comprise at least one of: butadiene-based polymer and copolymer latices, isoprene-based polymer and copolymer latices, copolymer latices prepared from styrene, and acrylic monomers, and polyurethane copolymers. The polymers of larger particle size may comprise vinyl acetate polymers. The polymer system may further comprise an inorganic granular particle with an average particle size above 500 nm. The polymer system may further comprise at least one of: alcohol ethoxylate surfactants, hydroxyethylcellulose, bronopol (C3H6BrNO4), and a silicone type antifoam. Such coating may provide improved donning characteristics in both wet and drive conditions.

After a final drying process is performed, the final article or glove is stripped from the former and inverted at operation 312. The gloves may then be removed by automation and readied for internal checks and final packing.

The described method provides a manufacturing process for gloves from many elastomeric synthetic rubbers, latices, and blends. It affords the ability to produce said gloves which closely mimics the physical properties of elastomeric gloves made from natural rubber latex at much lower palm thickness and glove weight, and without the allergenic-response issues associated with latex-protein. The described methods and compositions can be further advantageously incorporated into the manufacture of products free of Sulphur and other accelerators, thereby providing low dermatitis potential solutions whilst maintaining enhanced strength as measured by force at break values exceeding 6N and providing a market-leading level of protection and end-user safety.

Conclusion

Although many of the components and processes are described above in the singular for convenience, it will be appreciated by one of skill in the art that multiple components and repeated processes can also be used to practice the techniques of the present disclosure.

While the present disclosure has been particularly shown and described with reference to specific embodiments thereof, it will be understood by those skilled in the art that changes in the form and details of the disclosed embodiments may be made without departing from the spirit or scope of the disclosure. It is therefore intended that the disclosure be interpreted to include all variations and equivalents that fall within the true spirit and scope of the present disclosure.

What is claimed is:

1. An elastomeric rubber glove comprising:
   a substrate formed from a composition comprising:
      a synthetic rubber latex, and
      an ionic liquid, wherein the ionic liquid is encapsulated with surfactant prior to being compounded with the synthetic rubber latex.

2. The elastomeric rubber glove of claim 1, wherein the ionic liquid is present in the composition between 0.05 to 1.5 parts per hundred rubber.

3. The elastomeric rubber glove of claim 1, wherein the ionic liquid comprises a combination of one or more alkyl imidazole ionic salts selected from the group consisting of:
   1-Butylimidazole, 1-Methylimidazole, 1-Hexylimidazole, and Bromo-1-imidazole.

4. The elastomeric rubber glove of claim 1, wherein the composition further comprises one or more metal oxides, wherein the one or more metal oxides includes at least one of zinc oxide, magnesium oxide, cadmium oxide, and aluminum oxide.

5. The elastomeric rubber glove of claim 4, wherein the one or more metal oxides are present in the composition between 0 to 1.5 parts per hundred rubber.

6. The elastomeric rubber glove of claim 4, wherein the composition further comprises one or more functional materials, wherein the one or more functional materials include at least one of polycarbodiimides, aziridines, and epoxies.

7. The elastomeric rubber glove of claim 1,
   wherein the ionic liquid comprises 1-Butylimidazole, and
   wherein the composition further comprises a combination of one or more of the following: zinc oxide and aluminum oxide.

8. The elastomeric rubber glove of claim 1,
   wherein the substrate includes a single wall thickness of less than 0.10 mm in a palm region of the glove,
   wherein the substrate includes a modulus at 300% elongation (M300) lower than or equal to approximately 2.5 megapascals, and
   wherein the substrate includes a strength measured by a force at break exceeding 6 Newtons.

9. The elastomeric rubber glove of claim 1, further comprising a polymeric coating on an interior surface of the glove.

10. A wearable article comprising:
    a substrate formed from a composition comprising:
       a synthetic rubber latex, and
       an ionic liquid, wherein the ionic liquid is encapsulated with surfactant prior to being compounded with the synthetic rubber latex.

11. The wearable article of claim 10, wherein the ionic liquid is present in the composition between 0.05 to 1.5 parts per hundred rubber.

12. The wearable article of claim 10, wherein the ionic liquid comprises a combination of one or more alkyl imidazole ionic salts selected from the group consisting of:
    1-Butylimidazole, 1-Methylimidazole, 1-Hexylimidazole, and Bromo-1-imidazole.

13. The wearable article of claim 10, wherein the composition further comprises one or more metal oxides, wherein the one or more metal oxides includes at least one of zinc oxide, magnesium oxide, cadmium oxide, and aluminum oxide.

14. The wearable article of claim 13, wherein the one or more metal oxides are present in the composition between 0 to 1.5 parts per hundred rubber.

15. The wearable article of claim 13, wherein the composition further comprises one or more functional materials, wherein the one or more functional materials include at least one of polycarbodiimides, aziridines, and epoxies.

16. The wearable article of claim 10, wherein the protective article is an elastomeric rubber medical examination glove.

* * * * *